United States Patent [19]

Samain et al.

[11] Patent Number: 5,968,794
[45] Date of Patent: Oct. 19, 1999

[54] BIODEGRADABLE PARTICULATE VECTOR FOR TRANSPORTING MOLECULES HAVING BIOLOGICAL ACTIVITY

[75] Inventors: Daniel Samain; Ignacio De Miguel; Jaouad Meniali; Karim Ioualalen; Li Ding; Monique Cervilla, all of Toulouse; Valèrie Rieumajou, Astaffort; Pascal Delrieu; Laurent Imbertie, both of Toulouse, all of France

[73] Assignee: Biovector Therapeutics S.A., Labege, France

[21] Appl. No.: 09/012,645

[22] Filed: Jan. 23, 1998

Related U.S. Application Data

[63] Continuation of application No. 08/243,079, May 16, 1994, Pat. No. 5,736,371, which is a continuation of application No. 07/978,686, Apr. 2, 1993, abandoned.

[30] Foreign Application Priority Data

Jun. 4, 1991 [FR] France .................................... 91 06743
Jun. 4, 1992 [WO] WIPO ..................... PCT/FR92/00498

[51] Int. Cl.$^6$ .......................... C12N 11/12; A61K 38/43; C07K 1/04; C07H 1/02
[52] U.S. Cl. ...................... 435/178; 424/94.1; 424/94.4; 424/484; 424/488; 424/489; 424/499; 435/179; 514/2; 514/42; 530/402; 530/813; 530/814; 534/62; 534/109; 534/117
[58] Field of Search ..................... 435/179, 134, 435/178, 181; 424/94.4, 94.1, 484, 488, 489, 499; 514/2; 530/402, 813, 814; 536/62, 109, 117

[56] References Cited

U.S. PATENT DOCUMENTS

| | | | |
|---|---|---|---|
| 4,206,286 | 6/1980 | Keyes | 435/174 |
| 4,352,883 | 10/1982 | Lim | 435/178 |
| 5,080,833 | 1/1992 | Ishimori | 260/408 |
| 5,151,264 | 9/1992 | Samain et al. | 424/1.1 |
| 5,206,156 | 4/1993 | Samain et al. | 435/101 |
| 5,217,715 | 6/1993 | Krivan et al. | |

FOREIGN PATENT DOCUMENTS

| | | |
|---|---|---|
| 0344040 | 11/1989 | European Pat. Off. . |
| 0397227 | 11/1990 | European Pat. Off. . |
| 8911271 | 11/1989 | WIPO . |

*Primary Examiner*—David M. Naff
*Attorney, Agent, or Firm*—Burns, Doane, Swecker & Mathis, L.L.P.

[57] ABSTRACT

A biodegradable particulate vector for transporting biologically active molecules is prepared containing a nucleus formed of a cross-linked polysaccharide or oligosaccharide matrix having grafted ionic ligands, a layer of fatty acid compounds covalently bonded to the nucleus and a layer of phospholipids hydrophobically bonded to the layer of fatty acid compounds. Dextran, cellulose or starch may be cross-linked with epichlorohydrin to form a cross-linked polysaccharide matrix. Ionic ligands may be grafted using an acidic compound such as succinic acid, phosphoric acid or phosphorous oxychloride, or a basic compound such as choline, hydroxycholine, 2-(dimethylamino)ethanol or 2-(dimethylamino) ethylamine fastened onto the grafted acidic compound. Phosphoric acid or phosphorous oxychloride in one step provide both cross-linking and ionic ligands. Co-cross-linking can be obtained using a protein such as keratin, collagen or elastase. The vector may be prepared by reacting succinic acid monochloride with a cross-linked polysaccharide matrix to graft succinic acid onto the matrix to form the nucleus having ionic ligands, grinding the nucleus to a size between 10 μnm and 10 μm, drying, coupling fatty acid compounds to the nucleus and hydrophobically bonding phospholipids to the fatty acid compounds. After coupling the fatty acid compounds and before bonding the phospholipids, a molecule having biological activity may be added. The succinic acid monochloride is preferably prepared by reacting succinic acid dichloride with free succinic acid to form pure crystalline succinic acid monochloride.

25 Claims, No Drawings

BIODEGRADABLE PARTICULATE VECTOR FOR TRANSPORTING MOLECULES HAVING BIOLOGICAL ACTIVITY

This application is a continuation of application Ser. No. 08/243,079, filed May 16, 1994, now U.S. Pat. No. 5,736,371 which is a Continuation of application Ser. No. 07/978,686, filed Apr. 2, 1993, now abandoned; which corresponds to PCT/FR92/00498, filed Jun. 4, 1992.

BACKGROUND OF THE INVENTION

1. Field of the Invention

The present invention relates to a biodegradable particulate vector which is useful for transporting molecules having biological activity.

It also relates to a method of synthesis of this vector and of encapsulation of active principles in this vector.

Such vectors constitute one of the methods used for causing an active compound to enter or react inside a biological or biochemical system. Indeed, they must make it possible, in encapsulating such a compound, to protect it with respect to the normal agents of its catabolism, and to convey it to its site of activity, where the vector will release it.

2. Description of the Related Art

Liposomes, which consist of an aqueous vacuole surrounded by a phospholipid double-layer, have been used for this purpose. However, such a transportation system has a number of limitations due to the fragility of the liposomes, to their heterogeneity and to the complexity of their production on an industrial scale. Moreover, their transportation capacity is limited.

Another solution consists in using supramolecular biovectors (or SMBV), such as are described in the application PCT FR/8900229.

Such vectors comprise a central nucleus of crosslinked polysaccharides, surrounded by a first lipid layer bonded to the nucleus by covalent bonds, and by a second external lamella or layer of amphiphilic compounds.

These biovectors are very stable and are easy to lyophilize and sterilize, and their structure shows strong analogies to the natural vectors.

These biovectors can encapsulate active principles of different chemical natures, in accord with the characteristics of the three regions: a polar nucleus, a lipid corona and an amphiphilic external lamella.

However, these vectors display certain imperfections. Indeed, the level of active principle which can be encapsulated remains relatively low. Moreover, the active principle must be encapsulated at the time of the synthesis of the corresponding region of the biovector and, especially for the active principles encapsulated in the nucleus, there is a risk of detrimental change during the synthesis of the following layers.

It is thus desirable to have available particulate vectors which make it possible to charge active principles with quantitative yields, according to a procedure which makes it possible to preserve the structural integrity of the active principles, these vectors remaining, however, perfectly biodegradable and biocompatible with the body.

SUMMARY OF THE INVENTION

This is why the subject of the present invention is a biodegradable particulate vector, characterized in that it comprises:

- a nucleus consisting of a crosslinked polysaccharide or oligosaccharide matrix, onto which ionic ligands are grafted,
- a first semipermeable lipid layer, bonded to the nucleus by covalent bonds,
- a second layer of amphiphilic compounds, bonded to the first lipid layer by hydrophobic interactions.

Such a vector makes it possible to optimize the encapsulation of active principles inside the polysaccharide nucleus.

DETAILED DESCRIPTION OF THE INVENTION

These properties are obtained by grafting a large number of enzymatically hydrolyzable ionic ligands onto the crosslinked matrix. The nucleus, on which is thus conferred a significant ionic character, is then endowed with encapsulation properties far superior to those observed for the particulate vectors of the prior art, and it is completely biocompatible by the appropriate choice of these ligands and of the constituents of the matrix.

The ionic grafting must not be prejudicial to the stability nor to the size of the polysaccharide matrix. These ligands will thus preferably be chosen from biological molecules naturally present in the body and coupled to the matrix by enzymatically hydrolyzable bonds.

According to one of the aspects of the invention, the ligands grafted onto the matrix are acidic compounds. These acidic ligands can especially be chosen from succinic acid, phosphoric acid, citric acid, glycine, alanine, glutamic acid or aspartic acid.

Succinic acid is a natural constituent of the body and takes part in the Krebs cycle. It is a dicarboxylic acid which can form, with the hydroxyl groups of the polysaccharide matrix, an ester bond which is easily biodegradable by virtue of the ubiquitous presence in the body of succinylesterase. The acid functional group which is not involved in the ester functional group with the polysaccharide matrix thus remains available to provide the ion exchange properties.

The phosphates are also functional groups which are extremely common in the body. They are mainly found in association with lipids, sugars and nucleotides.

Monohydroxy or monoamino acids, for example citric acid, short-chain amino acids and acidic amino acids, can also be grafted onto the matrix.

It is advantageous to have available nuclei having a degree of grafting of ligands sufficient to make possible a satisfactory subsequent level of encapsulation. This degree must approach one charge per elementary sugar.

For example, particulate vectors are obtained in which succinic acid is grafted at a degree corresponding approximately to one charge per 1.5 glucose residues; or else phosphoric acid is grafted at a degree corresponding approximately to one charge per 1.5 glucose residues.

According to another aspect of the invention, the particulate vectors are characterized in that the ligands grafted onto the matrix are basic compounds, fastened onto the matrix via an acidic compound.

In order to obtain biodegradable grafting of basic ligands, the Applicant has found that it is possible to use especially succinic acid between the polysaccharide matrix and a basic compound. One of the acidic functional groups of succinic acid is used to produce a biodegradable ester functional group with the polysaccharide matrix and the other acidic functional group is used to produce an ester or amide functional group with the basic compound.

Preferably, the basic ligands grafted onto the matrix are bifunctional compounds containing a functional group which can by acylated, forming an amide or ester bond with an acidic compound fastened to the matrix.

The functional group which can be acylated is, for example, a hydroxyl or primary or secondary amine functional group.

The other basic functional group which cannot be acylated is, for example, a tertiary or quaternary amine functional group.

The basic ligand can especially be chosen from choline, hydroxycholine, 2-(dimethylamino)ethanol and 2-(dimethylamino) ethylamine.

Degrees of ionic grafting corresponding to one charge per three glucose residues can be observed.

The polysaccharide matrix, itself biodegradable, can consist of a chemically crosslinked polysaccharide chosen from dextran, starch, cellulose, oligosaccharides and their derivatives.

It can especially be produced by crosslinking a biodegradable polysaccharide, such as starch, with a bifunctional agent, such as epichlorohydrin. In the case where the epichlorohydrin/glucose ratio is maintained below 1/10, the gel obtained retains the property of being hydrolyzed by the amylases. The kinetics of hydrolysis are, however, slowed down when this ratio increases and approaches 1/10. Analysis of the products of enzymatic hydrolysis of the crosslinked starch matrices does not make it possible to reveal nonhydrolyzable glucose oligomers with a size greater than 10. The administration of such crosslinked starch matrices inside the body should thus not lead to the formation of glucose polymers which cannot be removed by the body.

It is also possible to crosslink a biodegradable oligo- or polysaccharide by direct reaction with phosphorus oxychloride or a derivative of phosphoric acid. The Applicant has found that it is possible to obtain phosphorylated polysaccharide matrices by virtue of the formation of phosphodiester bonds. In this case, the matrix is derived directly with negative charges, via the acidic functional groups of the phosphate formed.

It is also possible to co-crosslink the polysaccharide or oligosaccharide matrix with compounds such as proteins or peptides. It is necessary to mention, among the proteins which can be used: keratin, collagen, elastase, their derivatives and their analogs.

The nuclei of the particulate vectors according to the invention have a certain porosity, which depends on the crosslinking conditions, on the nature of the ionic ligand and on its degree of grafting.

The first semipermeable, lipid layer of the particulate vectors according to the invention preferably consists of natural fatty acids, fastened to a variable degree. Indeed, the density of this lipid layer can be adjusted by a controlled acylation. Control of the acylation reaction can be produced either by controlling the stoichiometry of the reactants or by controlling the reaction kinetics. The low density lipid layers make the particles only partially hydrophobic. It results therefrom that the particles have especially the ability of partially hydrating. The presence of the fatty acids placed at the periphery does not, however, enable the particles to disperse freely in the aqueous media and the weakly acylated nuclei are observed in the form of aggregates whose cohesion is due to hydrophobic-type bonds.

In a preferred embodiment, the particulate vector according to the invention can be characterized in that the second lipid layer consists of phospholipids or of ceramides.

The particles are then again completely dispersed. However, the optimum ratio between the weight of acylated nucleus and the weight of phospholipids to achieve a maximum dispersion is greater in the case of nuclei having a first semipermeable layer than in the case of completely hydrophobic nuclei.

It is possible that a double phospholipid lamella is formed around the acylated nucleus, the internal lamella being interdigitated by the fatty acids of the first lipid layer.

A particulate vector according to the invention can be characterized in that a molecule having biological activity is included in the nucleus.

Indeed, a vector according to the invention can encapsulate an active principle by profiting from the porosity of the nucleus. This nucleus preferably has a size of between 10 µm and 10 µm.

The active principles can enter the ionic polysaccharide nucleus through the semipermeable layer. They are then stabilized and maintained inside the nucleus by the establishment of coulombic bonds between their charges and the charges of the polysaccharide matrix.

The molecule having biological activity included in the particulate vector according to the invention preferably has a molecular weight of between 100 daltons and 500 kilodaltons.

Another subject of the present invention is a method of synthesis of a particulate vector having one or more of the above characteristics, this method being characterized in that:

a) a matrix is prepared by crosslinking a biodegradable hydrophilic polymer or oligomer, b) ionic ligands are fastened onto the matrix by enzymatically hydrolyzable bonds in order to obtain the nucleus of the vector, c) the nuclei are subjected to ultragrinding in order to bring them to a size of between 10 µnm and 10 µm, d) the nuclei are dried, e) lipid compounds are coupled chemically to the reactive functional groups at the surface of the nuclei in order to form the first layer, f) amphiphilic compounds in hydrophobic contact with the first layer are introduced in order to form the second layer.

The crosslinking of hydrophilic polymer, especially polysaccharide, is a method known to those skilled in the art. However, the conditions must be arranged to obtain a matrix which stays biodegradable and, preferably, does not give rise to products of enzymatic hydrolysis consisting of nonhydrolyzable glucose oligomers with a size greater than 10.

Grafting of the ionic ligands must make it possible to obtain a degree sufficient to confer an ionic character on the nucleus obtained.

In the case of succinic acid, the best results for grafting of succinic acid are obtained by using succinic acid monochloride. A novel method of synthesis of this reactant has been developed, using a transchlorination reaction between succinic acid dichloride and free succinic acid according to the following equation:

ClCO—CH$_2$—CH$_2$—COCl+HOCO—CH$_2$—CH$_2$—COOH→2 ClCO—CH$_2$—CH$_2$—COOH

This reaction is simple to carry out and leads to pure and crystalline monochloride with a good yield.

The advantage of this reactant with respect to the other reactants already described is:

1) its great ease of preparation
2) its very great chemical reactivity, especially with respect to hydroxyls 3) its solubility in water
4) the absence of toxic reaction by-products or residues.

The Applicant has found that the use of this reactant makes it possible to graft succinic acid onto polysaccharide (PS) matrices with good yields and under very gentle reaction conditions (0° C., pH 6.5). Degrees of ionic grafting corresponding to one charge per 1.5 glucose residues can especially be achieved.

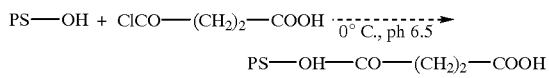

$$PS—OH—CO—(CH_2)_2—COOH$$

This reaction makes it possible to obtain a regular distribution of the grafted ligands on the polysaccharide matrix, in contrast to what is observed with the conventional techniques, with the use, for example, of succinic anhydride.

The coupling of phosphates on the PS matrices conventionally involves the reaction of phosphorus oxychloride ($POCl_3$) with the polysaccharide matrix in the presence of 2N NaOH. With the reaction conditions described, it is, however, not possible to obtain degrees of ionic grafting greater than one negative charge per six glucose residues. The Applicant has shown that the efficiency of this reaction can be significantly improved by working at low temperature and by controlling the temperature and pH reaction conditions during the reaction. Degrees of grafting corresponding to one charge per 1.5 glucose residues are thus obtained.

In another aspect, the invention can also be characterized in that Stages a) and b) can be carried out at the same time by virtue of the crosslinking ability of phosphorus oxychloride. Indeed, phosphorus oxychloride has the ability to form phosphodiester bonds between two polysaccharides making it possible, with a suitable control of the reaction conditions, to carry out the crosslinking and the introduction of negative charges at the same time.

When it is desired to graft basic ligands onto the matrix, an optimum method of preparation of the basic ligands is described below.

In order to obtain biodegradable grafting of basic ligands, it is possible to use succinic acid as intermediate compound between the polysaccharide matrix and a basic ligand.

The reaction is carried out by causing succinic acid dichloride to react stoichiometrically with the bifunctional compound. A coupling product is formed which has a reactive acid chloride functional group and a basic, tertiary or quaternary amine functional group.

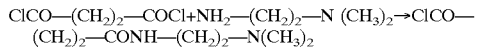

The basic functional group makes it possible for the reactant to be soluble in water and provides ion exchange properties. The acid chloride functional group makes it possible to carry out grafting onto the hydroxyls of the glucoside matrix.

It has been possible to obtain degrees of ionic grafting corresponding to one positive charge per 1.5 glucose residues with these reactants, or even, for example, one charge per 3 glucose residues.

The reaction described above can also be used for grafting monohydroxy or monoamino acids onto the glucoside matrix onto the glucoside matrix (sic).

In all cases, the degree of ionic grafting of the polysaccharide matrix is variable, and will be adjusted especially depending on the type of compound to be encapsulated; vectors can be used for which the degrees of grafting are less than those mentioned above as being able to be obtained by the methods described.

In particular, degrees of ionic grafting of the order of 1 charge per 3 glucose residues will be used.

The ionic nuclei can be ultraground by techniques analogous to those used for the neutral polysaccharide matrices, such as high pressure extrusion or ultrasound. The size of the particles can be adjusted by regulating the ultragrinding conditions and the state of hardness of the gel, which depends on the crosslinked character and the ionic state of the nucleus.

Drying of the nuclei must avoid their aggregation as much as possible. This can be obtained especially by carrying out Stage d) in the presence of ammonium bicarbonate.

Indeed, it is possible to reduce the degree of aggregation during the drying operations, by freeze drying or atomization, by adding ammonium bicarbonate ($NH_4HCO_3$) to the suspensions to be dehydrated. This highly water-soluble compound in effect maintains a certain ionic force between the particles which prevents them from coming together and thus prevents their possible aggregation. Ammonium bicarbonate, being volatile, is then removed during drying and does not interfere with the following operations. The use of ammonium bicarbonate makes it possible to obtain particulate powders characterized by a much lower density than in the absence of bicarbonate. The Applicant has found that the reduction of aggregation phenomena manifested itself on an increase in the degree of acylation of the particles and in a greater hydrophobicity of the latter.

The synthesis of the semipermeable lipid layer is a regioselective synthesis which is carried out by an acylation of the polysaccharide nuclei in an aprotic medium which is not a solvent of the polysaccharides. The Applicant has found that, among the solvents which are useful for this reaction, it is possible to use $CO_2$ in the supercritical state to carry out Stage e).

The use of $CO_2$ in the supercritical state represents a significant improvement since this compound is nontoxic and can be entirely removed at the end of the reaction by reduction in pressure of the reaction atmosphere.

Moreover, the Applicant has found that it is possible to reduce the density of the lipid layer by a controlled acylation. Control of the acylation reaction can be carried out either by controlling the stoichiometry of the reactants or by controlling the reaction kinetics.

Moreover, the Applicant has found that, especially in the case of polysaccharide nuclei of very small size (<100 nm), the homogeneity of the lipid grafting can be improved by carrying out two or more successive acylation Stages f) separated by rehydration and drying stages E).

The aggregation phenomena are, indeed, more difficult to remove in the case of small particles; a residual aggregation will result in a nonhomogeneous acylation of the surface of the particle, leading to the presence of acylated and nonacylated parts of the surfaces of the polysaccharide nuclei.

When such particles are suspended in water, the lipid parts join to each other enabling the nonacylated parts to be re-exposed.

A second acylation cycle then makes it possible to acylate the parts of the surfaces of the polysaccharide nuclei which were not acylated during the first cycle.

In one of the preferred aspects of the present invention, the method of synthesis of the particulate vector is characterized in that, after Stage e) and before Stage f), substances having biological activity are included in the nucleus.

One of the disadvantages of the SMBV described in the original patent was the possibility of derivatizing the encapsulated product by fatty acids when the acylation reaction was carried out after the encapsulation.

The Applicant has found that it is possible to cause the active principles to enter the ionic polysaccharide nucleus through the semipermeable layer and to thus avoid derivatization of the active principles. Once the active principles have passed through the semipermeable lipid layer, they are stabilized and maintained inside the nucleus by establishment of coulombic bonds between their charges and the charges of the polysaccharide matrix.

Moreover, practically quantitative encapsulation yields can be obtained by using a method which consists in progressively hydrating an active principle mixture (sic) with the acylated nuclei obtained at the end of Stage e). The hydration being (sic) either by water, or by a buffer, or by a water/lower alcohol mixture.

It is possible that the encapsulation is favored by the saturating concentrations of active principles thus obtained and by the flow of the liquid towards the internal part of the particles induced by their hydration.

In the case where the substance having biological activity is a nonionic compound, the method according to the invention can be characterized in that an ionic charge is reversibly grafted onto the said substance before its inclusion in the nucleus.

Indeed, the Applicant has found that it is possible to encapsulate polar, nonionic active principles inside ionic nuclei by reversibly grafting an ionic charge onto them. We have found that this reversible grafting can be carried out especially by the reaction of the hydroxyls of the active principles with succinic acid monochloride. There is thus formed a monosuccinate of the active principle which has a negative charge. The original active principle is then regained by the action of succinylesterase.

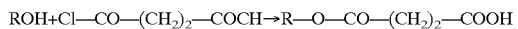
ROH+Cl—CO—(CH$_2$)$_2$—COCH→R—O—CO—(CH$_2$)$_2$—COOH

In one of the modes of implementation of the method according to the invention, the latter can be characterized in that Stage f) is carried out by dispersion of the acylated nuclei obtained at the end of Stage e), in which nuclei is optionally included an active principle, in a lipid medium containing triglycerides and phospholipids, and then by treatment with a lipase. The hydrophobic character of the nuclei having a semipermeable lipid layer is sufficient to make it possible for them to disperse in lipid environments such as triglycerides. These dispersions can be compared with stabilized water/oil emulsions.

In another of the modes of implementation of the method according to the invention, the latter can be characterized in that, for nuclei of very small size (<50 nm), Stage f) is carried out by dispersion of the acylated nuclei obtained at the end of Stage e), in which is optionally included an active principle, in an aqueous dialyzable detergent solution, whose molarity is greater than the critical micellar concentration.

The Applicant has found that it is possible to mix the suspension obtained with a dispersion of amphiphilic compounds, such as phospholipids or cholesterol, in the same detergent solution and to obtain the SMBV by rapid dilution of the suspension in order to bring the detergent to a molarity less than the CMC, followed by an extensive dialysis stage to remove the detergent.

The Applicant has shown especially that it is possible to establish, in a stable way, a phospholipid layer around the nuclei which have a semipermeable lipid corona.

The combination of this phospholipid layer with the acylated nuclei was revealed by chromatographic analysis of the corresponding SMBV and the perfect superposition of the chromatographic profiles of fluorescent markers grafted covalently onto the nucleus or combined with the phospholipids.

The Applicant has shown that the acylated nuclei can moreover be incorporated into formulations of the oily compounds and especially in emulsions. The system obtained is thus equivalent to a water/oil/water triple emulsion.

The Applicant has, moreover, found that the treatment of an oil/water emulsion, whose oily part is composed of a mixture of short-chain triglycerides, phospholipids and acylated nuclei, by a lipase leads, after enzymatic hydrolysis of the triglycerides and dialysis, to the preparation of SMBV composed of acylated nuclei surrounded by phospholipids.

The particulate vectors according to the present invention can be used for incorporating any type of active chemical molecule, as was described in the abovementioned patents.

The active principles can be, for example, pharmaceutical and/or cosmetic active principles, such as keratin, which is (sic) incorporated in the nucleus.

The following examples are intended to illustrate the invention without in any way limiting its scope and reveal certain types of molecule which can be incorporated into the vectors according to the invention.

EXAMPLE 1

Preparation of Biodegradable Polysaccharide Matrices 500 g of amylopectin (Roquette, Lille, France) are solubilized in one liter of 2N NaOH in a 5 l reactor. When the solution is very homogeneous, 28 g of epichloroydrin (sic) (Fluka, Switzerland), corresponding to 0.1 equivalent/glucose residue, are introduced. After the end of addition, the preparation is homogenized for a further 1 h and then left standing for 8 h. The preparation of polymerized starch is then brought to pH 7 by addition of 2N acetic acid and then crudely dispersed using a helical pulverizer. The gel obtained is then filtered on a Büchner and washed several times with distilled water until all the salts and the reaction by-products have been removed. After freeze drying, 450 gr (90%) of crosslinked gel are obtained.

EXAMPLE 2

Enzymatic Degradation of the Crosslinked Starch Gel 1 g of crosslinked starch according to Example 1 is dispersed in 50 ml of phosphate buffer pH 6.9 and brought together with 200 units of Bacillus (Sigma) amylase. The reaction mixture is stirred for one hour at 20° C. and then reaction is halted by heating at 90° C. for 2 min. The reaction mixture has become clear and the reaction products are analyzed by HPLC on a C18 column with an entirely aqueous mobile phase and detection by refractive index. The results obtained are compared with those obtained with non-crosslinked starch and show there is no appearance of oligomers with a size greater than 10.

EXAMPLE 3

Preparation of Ionic Polysaccharide Matrix Grafted by Succinic Acid a) Preparation of Succinic Acid Monochloride:Cl—CO—(CH$_2$)$_2$—COOH 50 g of succinic acid are dispersed in 50 ml of an anhydrous solution of THF and DMF (90/10) maintained at 0° C. The stoichiometric quantity of succinic acid dichloride (66 g) is added progressively with stirring. The reaction is accompanied by heat evolution and the reaction mixture is severely cools (sic) in order to keep the temperature below 0° C. The reaction is continued until the succinic acid in suspension has completely dissolved. The progressive precipitation of the succinic acid monochloride is observed simultaneously with the dissolution of the succinic acid.

After the end of the reaction, the monochloride is completely precipitated by addition of anhydrous petroleum ether (100 ml) and separated from the reaction mixture by filtration on a Büchner. After the precipitate has been washed with 100 ml of anhydrous petroleum ether and dried in a desiccator under reduced pressure, 80 g of pure monochloride are obtained (yield 70%).

b) Characterization of Succinic Acid Monochloride

| Elemental analysis Values calculated experimental: (sic) | | |
|---|---|---|
| C | 35% | 36% |
| H | 3.6% | 3.4% |
| O | 35% | 36.5% |
| Cl | 26% | 24.1% |

Infrared spectrum: bands at 3200 $cm^{-1}$ (s) (OH), 1800 (s) (COCl).

Characterization of Succinic Acid Monochloride by the Formation of N-phenylsuccinamic Acid:($C_5H_5$)—NH—CO—$(CH_2)_2$—COOH 100 mg of succinic acid monochloride are dissolved in 2 ml of anhydrous acetonitrile. 1.5 equivalents of aniline (102 mg) are added at room temperature and the reaction mixture is kept stirred for 30 minutes. 100 ml of 0.005M sulfuric acid are then added and the solution is extracted with ethyl ether (3×3 ml). The ether phases are combined and washed with water to neutrality and then dried over anhydrous $MgSO_4$. The ether is then filtered and evaporated under reduced pressure to give 90 mg of N-phenylsuccinamic acid.

Chromatographic analysis is carried out on a 5 μm C8, 3.6 cm×4.6 mm ID, column with UV detection at 254 nm. The column is developed by a linear gradient between a 5 mM TFA mobile phase and a 5 mM TFA/acetonitrile (30/70) mobile phase. The chromatogram shows the presence of a single peak characterized by a K' of 13.5. No peaks corresponding to the elution of aniline or of the dianilide derivative of succinic acid are observed.

Infrared spectrum: bands at 3300 $cm^{-1}$ (s) (OH), 1770 $cm^{-1}$ (s) (COOH), 1650 $cm^{-1}$ (s) (CON).

| Elemental analysis Values calculated experimental: (sic) | | |
|---|---|---|
| C | 62.5% | 64% |
| N | 7.3% | 6.9% |
| H | 5.2% | 5.7% | c) Grafting of Succinic Acid onto the Crosslinked Starch Matrix 100 g of Crosslinked starched prepared according to Example 1 are dispersed in 1 liter of a 2M NaCl solution and cools (sic) to 0° C. Succinic acid monochloride (85.3 g), in the powder form, is then added progressively to the dispersion which is gently stirred and held at a pH of 6.5 and below 0° C. After the end of addition, the reaction mixture is stirred for a further one hour at 0° C. and then 2 H at room temperature. The reaction mixture is then acidified to a pH of 2 by addition of 2N HCl and stirred for one hour. The ionic gel obtained is separated from the reaction mixture by filtration on a Büchner and washed several times with distilled water to neutrality. After freeze drying, 110 gr (yield 78%) of ionic gel are obtained. The degree of ionic grafting is measured by titrating the gel with a 0.1M NaOH solution with phenophthalein (sic) as indicator. One negative charge per 2.5 glucose residues is obtained.

EXAMPLE 4

Preparation of Polysaccharide Matrices Grafted by Phosphoric Acid 100 g of crosslinked starch obtained according to Example 1 are dispersed in a 2M NaCl solution, pH 13.5, and cools [sic] to 0° C. Phosphorus oxychloride (114 ml, 104 g) is added progressively while maintaining the pH at 13.5 and the temperature below 0° C. After the end of addition, the reaction mixture is stirred for a further two hours while being left to return to room temperature. The mixture is then acidified to a pH of 2 by addition of 2N HCl, stirred for one hour, filtered on a Büchner and washed with distilled water to neutrality. After freeze drying, 110 gr (yield 90%) of ionic gel are obtained. The degree of grafting obtained is determined by titrating with 0.1N sodium hydroxide solution with phenolphthalein as indicator. One negative charge per 1.5 glucose residues is found.

EXAMPLE 5

Preparation of Polysaccharide Matrix Grafted by N-[2-(Dimethylamino) Ethyl]Succinamoyl a) Preparation of N-[2-(Dimethylamino)Ethyl]Succinamic Acid: Cl—CO—$(CH_2)_2$—CO—NH—$(CH_2)_2$—N $(CH_3)_2$)

15.4 g of succinic acid dichloride are dissolved in 100 ml of anhydrous acetonitrile and the solution is kept stirring at 0° C. A solution of 10 g of 2-(dimethylamino) ethylamine in 100 ml of anhydrous acetonitrile is added dropwise. The reaction mixture is then stirred for 30 min after the end of addition while maintaining the temperature at 0° C. The coupling product is then precipitated in the round-bottomed reaction flask. When all the product has been precipitated, it is separated from the reaction mixture by filtration on a Büchner, washed several times with cold acetonitrile and then dried in a desiccator under reduced pressure to give 18 g of pure product (yield 84%).

| Elemental analysis Values calculated experimental (sic) | | |
|---|---|---|
| C | 46.7% | 48% |
| N | 13.6% | 12.5% |
| H | 6.8% | 7.6% | b) Grafting of N-[2-(Dimethylamino)Ethyl] Succinamic Acid onto a Glucoside Matrix 100 g of crosslinked starch according to Example 1 are dispersed in one liter of 2M NaCl kept stirring at a pH of 6.5 and at 0° C. 63.4 g of N6[2-(dimethylamino)-ethyl] succinamoyl chloride (sic) are then added progressively. When all the acid chloride has been added, the mixture is left to stir for a further 2 h at 0° C. The ionic gel obtained is then filtered on a Büchner, washed with distilled water and freeze dried to give 105 g of basic matrix (yield 93%). The degree of grafting obtained is determined by analysis of the nitrogen content present in the gel (3.6%). This degree of grafting corresponds to one positive charge per 4 glucose residues.

EXAMPLE 6

Preparation of Ionic Polysaccharide Particles of Small Size a) Particles Grafted with Succinic Acid 100 gr of ionic gel obtained according to Example 3 are dispersed in 4 liters of distilled water and homogenized for 1 H with a Rannie homogenizer (industrial model 12.S1) at a pressure of 1000 bars and a flow rate of 80 1/h.

Analysis of the size of the particles obtained is carried out using a Coulter N4 nanosizer and shows that 90% of the particles have a diameter of less than 50 nm.

The particles of very small size are then dried by freeze drying or by atomization in the presence of ammonium bicarbonate (50 gr/l). After drying, the size of the particles is monitored again on the nanosizer after dispersion of the particles in water. The results obtained are identical to the values obtained before drying. The degree of ionic grafting is also identical.

b) Particles Grafted with Phosphoric Acid 100 g of the phosphorylated gel obtained according to Example 4 are dispersed in 10 l of distilled water and homogenized using a Rannie 12-51 H homogenizer. The homogenization pressure is 900 bars and the flow rate is 80 l/h.

There is obtained a fluid suspension of acidic crosslinked polysaccharide nanoparticles whose size, measured by a Coulter N4MD nanosizer, is centered around 20 nm. The nanoparticles are then dried by freeze drying in the presence of 50 g/l of ammonium carbonate.

EXAMPLE 7

Preparation of the Semipermeable Lipid Layer 10 gr of 50 nm particles obtained according to Example 6(a) are dispersed in 30 ml of dichloromethane. 0.8 gr of palmitoyl chloride is added. A reflux condenser equipped with a potassium carbonate guard is fitted onto the reaction flask and the reaction mixture is stirred vigorously at reflux overnight. The dichloromethane is then evaporated with a rotary evaporator and the residue is washed several times with ethanol and then dried under vacuum. 10.3 g of acylated particles (yield 100%) are obtained. The degree of grafted fatty acids measured after saponification of the particles is 5%. With the same acylation conditions, the degree of fatty acids grafted onto particles which are identical but dried without ammonium bicarbonate is 3%.

EXAMPLE 8

Preparation of the Semipermeable Lipid Layer by Multiple Acylation 10 g of 20 nm particles obtained according to Example 6(b) are dispersed in 30 ml of dichloromethane. 1.7 g of palmitoyl chloride is added. A reflux condenser equipped with a potassium carbonate guard is fitted onto the reaction flask and the reaction mixture is stirred vigorously at reflux overnight. The dichloromethane is then evaporated with a rotary evaporator and the residue is washed several times with ethanol and then dried under vacuum. 10.3 g of acylated particles (yield 98%) are obtained. The degree of grafted fatty acids measured after saponification of the particles is 5%. With the same acylation conditions, the degree of fatty acids grafted onto particles which are identical but dried without ammonium bicarbonate is 3%.

10 g of the acylated particles obtained are resuspended with vigorous stirring in 1 liter of water. Once the dispersion is homogeneous, the particles are again dried in the presence of ammonium bicarbonate according to Example 6.

The particles are dispersed in 30 ml of dichloromethane and reacylated according to the procedure described above. After washing, 9.5 g of particles (yield 94%) are obtained with a degree of fatty acids measured at 6%.

A third reaction cycle, comprising all the stages already described (hydration, freeze drying and reacylation) leads to 9 g of acylated particles (total yield 88%) with a degree of fatty acid of 6.5%.

EXAMPLE 9

Characterization of the Lipid Layer

A1—Preparation of White SMBV 10 mg of 20 nm, acylated, phosphate cores, prepared according to Example 8, are dispersed in 1 ml of 50 mM Octyl Glucopyranoside OGP (Fluka). They are mixed under ultrasound with an 80/20, 5 mg solution of purified egg yolk Lecithins (Sigma) and Cholesterol (Sigma) dispersed in 1 ml of 50 mM OGP. This preparation is then crudely diluted to 10 mM under ultrasound and then dialyzed extensively for 48 hours.

A2—Preparation of Fluorescent SMBV Labeled With Rhodamine a—Preparation of Fluorescent Acylated Cores Labeled with Rhodamine 50 mg of 20 nm, acylated, phosphate cores, prepared according to Example 8, are dispersed in 1 ml of pH 10 100 mM Sodium Bicarbonate (Sigma). 0.5 mg of Rhodamine B Isothiocyanate (Sigma), solubilized in Dimethylformamide (SDS), is added, i.e. 1% of Rhodamine with respect to the weight of acylated nuclei. After stirring for 12 hours at room temperature, several washings with ethanol are carried out in order to remove the unreacted Rhodamine. The acylated cores are then dried by freeze drying.

b—Establishment of the Phospholipid Lamella

* From Fluorescent Cores 100 mg of fluorescent acylated cores are dispersed in 2 ml of 50 mM Octyl Glucopyranoside OGP (Fluka). 5 mg of an 80/20 mixture of purified egg yolk Lecithins (Sigma) and Cholesterol (Sigma) dispersed in 1 ml of 50 mM OGP, i.e. 50% of phospholipid mixture with respect to the weight of acylated nuclei, is then introduced into this suspension. This solution is then crudely diluted to 10 mM under ultrasound and then dialyzed extensively for 48 hours. Two other preparations are also carried out using respectively 20 mg and 30 mg of phospholipid mixture, i.e. 200 and 300% of phospholipids with respect to the weight of acylated nuclei.

* From Fluorescent Phospholipids

The SMBV are prepared in an identical manner but with nonfluorescent acylated cores and by introducing 1% of phospholipids labeled with Rhodamine (Molecular Probe) into the purified egg yolk Lecithins/Cholesterol mixture.

c—Preparation of Reference Fluorescent Liposomes 5 mg of egg yolk Lecithins/Cholesterol (80/20), containing 1% of Phospholipids labeled with Rhodamine, are dispersed in 1 ml of 50 mM OGP. The solution is crudely diluted to 10 mM under ultrasound and then dialyzed extensively for 48 hours.

B1—Analysis of the Size of the SMBV

Analysis of the size of the white SMBV is carried out using a Coulter N4 nanosizer and shows that 99% of the particles have a diameter of 20 nm (+/−2 nm).

This measurement stays unchanged after storing for 3 months at 4° C.

B2—HPLC Analysis by Gel Permeation

The SMBV are detected by fluorescence (280 nm excitation—580 nm emission) on a TSK G 6000 PW column in 10 mM Tris/120 mM NaCl as solvent.

There is observed, for the SMBV with fluorescent cores having 50% phospholipids, a peak corresponding to an elution volume of 7.5 ml.

Analysis of the SMBV having 50% fluorescent phospholipids makes it possible to obtain a peak having exactly the same elution volume, 7.5 ml.

Analysis of the fluorescent liposomes makes it possible to reveal a peak having an elution volume of 9.9 ml, markedly different from the peak of the SMBV.

Analysis of the SMBV having 200 and 300% phospholipids makes it possible to reveal two peaks, one at 7.5 ml and the other at 9.9 ml. The peak at 9.9 ml has an intensity which increases with the percentage of phospholipids.

The results clearly show that the phospholipids are indeed combined with the acylated cores. Moreover, they show that there exists a phospholipid optimum for establishing the amphophilic layer and that, beyond that, liposomes are observed which correspond to the excess phospholipids.

Moreover, it is noted that the chromatographic profile of the SMBV is unchanged after several weeks, whereas that of the liposomes changes over several days, which seems to indicate a greater stability of the SMBV.

EXAMPLE 10

Charging of Butirosin to SMBV Containing Succinylated Ionic Nuclei and Having a Semipermeable Lipid Layer Butirosin is an antibiotic of the aminoglycoside family. It is a molecule consisting of an aminocyclitol bonded by glycoside bonds to amine-containing sugars. It is thus a very polar and basic product which is soluble only in water. Its molecular weight is 556.

Acylated acid nuclei which are 50 nm in size are first prepared according to Example 7. 1 g of acylated nuclei are mixed, in the dry state, with 1 g of butirosin base (Park-Davis). The mixture is then hydrated very progressively by addition of distilled water. The mixture is kept constantly so stirred and at 50° C. 10 ml of water are then added while leaving the mixture to return to room temperature and the mixture is left to stir for a further 2 h.

The suspension obtained is then freeze dried. The dry residue is dispersed in 5 ml of ethanol and added dropwise to a suspension of unilamellar liposomes (1.5 g of purified egg yolk lecithins in 50 ml of distilled water). After being subjected to ultrasound in a bath for ½ h, the suspension is ultrafiltered (cutoff point 7500 daltons) and the free butirosin present in the ultrafiltrate is quantitatively determined by HPLC. The results show the presence of 50 mg of butirosin in the ultrafiltrate, which corresponds to an incorporation yield of 95% and a degree of incorporation of 95% by weight of butirosin with respect to the weight of the acylated core.

EXAMPLE 11

Charging of Butirosin to SMBV Containing Phosphorylated Ionic Nuclei and Having a Semipermeable Lipid Layer In a first step, acylated acidic nuclei with a size of 20 nm are prepared according to Example 8. 50 mg of acylated nuclei are then mixed with 25 mg of butirosin base (Park-Davis) diluted in 1 ml of distilled water. The mixture is kept constantly stirred at room temperature overnight.

The suspension obtained is dispersed in the presence of Octyl-d-Glucopyranoside (sic) (OGP) (Fluka) to a final molarity of 50 nM and is added dropwise to a solution of phospholipids (50 mg of a mixture of purified egg yolk lecithins/cholesterol (80/20) w/w, dispersed in 10 ml of 50 mM OGP). After being subjected to ultrasound in a bath for 10 minutes, this solution is crudely diluted under ultrasound to a molarity of 5 mM in OGP and is then ultrafiltered (cutoff point: 30,000 daltons). Size analysis carried out on a nanosizer (Coulter N4 SD) shows that 99% of these SMBV have a diameter of 20 nm (+/−2 nm).

The free butirosin present in the filtrate is quantitatively determined by microbiology. The concentration of the antibiotic is determined by measuring the area of inhibition of the growth of *Bacillus subtillis* (ATCC 6633). The results show the presence of 2.5 of free butirosin in the ultrafiltrate, which corresponds to an incorporation yield of 90% of butirosin and to a degree of incorporation of 45% by weight of butirosin with respect to the weight of acylated cores.

EXAMPLE 12

Charging Horseradish Peroxidase to the SMBV Containing Acidic Nuclei and Having a Semipermeable Lipid Layer Horseradish peroxidase is a basic enzyme which has a molecular weight of 40,000 daltons. The acylated acidic nuclei prepared according to Example 7 are used. One g of acylated nuclei is mixed, in the dry state, with 1.5 g of peroxidase (Fluka). The mixture is stirred and hydrated very progressively by addition of distilled water. The temperature is maintained at 40° C. 10 ml of distilled water are then added and the mixture is left to stir for a further 2 h at 40° C. 10 ml of a suspension of 400 mg of octyl glucoside and 1.5 g of purified egg yolk lecithin are then added and the resulting mixture is subjected to ultrasound for ½ h in a bath while keeping the temperature below 30° C. The suspension obtained is then dialyzed for 24 h at 4° C. against distilled water so as to remove the octyl glucoside. The preparation is then ultrafiltered with a membrane having a cutoff point at 100,000 daltons. The free peroxidase is quantitatively determined in the ultrafiltrate by the Bradford method and by enzymatic quantitative determination. The results via the two methods show the presence of 45 mg of free peroxidase, i.e. an encapsulation yield of 97% and a degree of charging of 145% with respect to the weight of acylated nuclei.

EXAMPLE 13

Preparation of Acylated Basic Nuclei with a Size of 50 nm

The basic nuclei are prepared by grafting N-[2-(dimethylamino)ethyl]succinamic acid according to Example 5. 200 g of basic PS matrix are dispersed in 2 l of distilled water and ultraground at high pressure (800 bars) with a Rannie homogenizer to give particles with a size of 50 nm. These particles are atomized in the presence of ammonium bicarbonate (50 g/l) to give 130 g of dry powder which are suspended in 400 ml of dichloromethane. 16 g of oleoyl chloride and then added and the mixture is left stirring at 24 h at room temperature. The acylated particles obtained are then separated from the reaction mixture by centrifuging and are washed with dichloromethane and then with ethanol. The final ethanol suspension is evaporated under vacuum while cold to give 125 g of acylated basic nuclei. The degree of grafting of fatty acids is measured by quantitative determination of the free oleic acid after saponification of the particles. A degree of 4.5% is found.

EXAMPLE 14

Charging of a Nucleotide: Adenosine 5'-Monophosphate (AMP)

AMP is an acidic molecule with a molecular weight of 347. Charging is thus carried out on basic nuclei.

50 mg of basic nuclei, prepared according to Example 13, are mixed with 10 mg of AMP (Fluka) diluted in 1 ml of distilled water. Incorporation is carried out with stirring at room temperature for 3 hours. The suspension obtained is then dispersed in the presence of Octyl-d-Glucopyranoside (sic) (OGP) to a final molarity of 50 mM and is added dropwise to a solution of phospholipids (50 mg of a purified egg yolk lecithins/cholesterol (80/20) w/w mixture, dispersed in 10 ml of 50 mM OGP). After being subjected to ultrasound in a bath for 10 minutes, the solution is crudely diluted under ultrasound to a molarity of 5 mM in OGP and is then ultrafiltered (cutoff point: 30,000 daltons). Size analysis carried out on a nanosizer (Coulter N4 SD) shows that 99% of these SMBV have a diameter of 50 nm (+/−3 nm).

The free AMP is quantitatively determined by spectrophotometry. The results obtained show a value of 0.5 mg of IMP, i.e. incorporation yield of 95% and a degree of charging of 19% with respect to the weight of acylated nuclei.

EXAMPLE 15

Charging of Stachyose, a Nonionic Molecule

Stachyose is a tetrasaccharide with the structure Gal-[1→-6]-Gal-[1→-6]-Glc-[1→-2]-Fru. It is a compound which is free of electrical charge and is very polar. The structure of stachyose does not therefore permit it to be encapsulated in one of the polar or lipophilic compartments of the SMBV. We have carried out the encapsulation by grafting, to the stachyose molecule, an acidic ionic functional group coupled to a hydroxyl of the stachyose by an enzymatically hydrolyzable ester functional group.

a) Preparation of the Acidic Derivative of Stachyose 1 g of stachyose is dissolved in 5 ml of an aqueous solution kept stirring at 0° C. and at a pH of 6.5 by a pH stat. 135 mg of succinic acid monochloride, prepared according to Example 3, are added progressively to this solution. After the end of addition, the mixture is left to stir for a further 2 h while allowing to return to room temperature. The reaction mixture is applied to the top of a G25 gel permeation column and eluted with distilled water. The fractions containing the oligosaccharide (tested by the Dubois method) are combined and freeze dried to give 0.85 g of modified stachyose. The degree of ionic grafting is measured by titrating with 0.1N sodium hydroxide solution and corresponds to one ionic charge per 4.2 sugars and thus approximately one charge per molecule of stachyose.

b) Charging of the Modified Stachyose 50 mg of acylated basic nuclei, prepared according to Example 10, are intimately mixed, in the dry state, with 25 mg of modified stachyose. The mixture is then hydrated very progressively with 1 ml of distilled water, while constantly stirring and at room temperature for 3 hours. The suspension obtained is dispersed in the presence of Octyl Glucopyranoside OGP (Fluka) to a final molarity of 50 mM. It is then added dropwise to a preparation of Phospholipids (50 mg of purified egg yolk Lecithins/Cholesterol (80/20) in 10 ml of 50 mM OGP). After being subjected to ultrasound for 10 minutes in a bath, the preparation is crudely diluted to 10 mM. After being subjected to ultrasound for 10 minutes in a bath, the preparation is crudely diluted to 10 mM under ultrasound (sic), then ultrafiltered and the free stachyose is quantitatively determined by the Dubois method. The results show a value of 2.5 mg of stachyose in the ultrafiltrate, i.e. an encapsulation yield of 90% and a degree of charging of 45% with respect to the weight of acylated nuclei.

Analysis of the size is carried out using a Coulter N4 nanosizer and shows that 98% of the particles have a diameter of 50 nM (sic) (+/−3 nm).

EXAMPLE 16

Preparation of SMBV from a Dispersion of Acylated Nuclei in a Solution of Triglycerides 15 mg of polysaccharide nuclei (50 nm), prepared according to Example 7, are dispersed in a mixture of 30 mg of purified egg yolk lecithins and 250 mg of tributyrin. The mixture is taken up in 10 ml of pH 7.2, 0.1 Tris-maleate buffer and the suspension is homogenized using a Vortex and by magnetic stirring. The whole is placed on a water bath at 37° C. and 25 mg of lipase (Type VII, C. Cylindrae (sic), Sigma) are added. The butyric acid released is neutralized by addition of 0.01M NaOH using a pH stat which maintains the pH at 7.2. After incubation for 30 min, the suspension has become clear and measurement of the sizes (Coulter N4SD, Coultronics) shows a population with a size centered around 50 nm. The suspension is then transferred into a dialysis bag (Cut-off 12,000–14,000, Spectrapor), placed in one liter of pH 7.2, 0.01M tris-maleate buffer and left overnight to dialyze. Analysis, by gas phase chromatography, of the solution contained in the dialysis bag shows the absence of tributyrin and butyric acid.

EXAMPLE 17

Preparation of Acylated Nuclei in Super-Critical $CO_2$ 0.3 g of ionic polysaccharide nuclei, prepared according to Example 6, are placed in a 10 ml, sapphire reactor tested to 150 bars. 60 mg of oleoyl chloride are added and the reactor is pressurized to 100 bars with anhydrous $CO_2$. The reaction mixture is then maintained under stirring for 12 h at 40° C. The $CO_2$ is then released, the residue is washed several times with ethanol and then dried under vacuum at low temperature. 0.25 g of acylated particles is obtained. The degree of grafted fatty acid (sic) measured after saponification of the particles is 6%.

EXAMPLE 18

Preparation of Hydrophilic Matrices by Crosslinking of Oligosaccharides with Phosphorus Oxychloride 50 g of dextrin 10 (Fluka) (molecular weight 1620), which are dissolved in 45 ml of water containing 1 g of sodium borohydride, are introduced into a 500 ml, round-bottomed flask.

The reaction mixture is stirred for two hours at room temperature until the end reducing sugars have been completely reduced, in order to prevent undesirable enolization reactions of the polysaccharides in basic medium.

Once the temperature is stabilized at 0° C., 24 g of phosphorus oxychloride ($POCl_3$, 0.15 M (sic)) are added dropwise with vigorous stirring. At the same time, 57 ml of 10M NaOH are added so that the addition of the reactants is performed simultaneously.

After the end of addition of the reactants, the reaction mixture is gently stirred for a further 1 hour and then neutralized to a pH of 7 by addition of acetic acid.

The gel thus obtained is then crudely dispersed using a helical pulverizer, filtered on a Büchner and washed several times with distilled water until the salts and reaction by-products have been removed.

The gel is finally precipitated with ethanol and dried under reduced pressure to produce 40 g of crosslinked dextrin (80% yield).

Titration of 1 g of crosslinked gel using an automatic titrimeter (Titroprocesseur Methrom 682) shows a neutralization volume of 1.8 mEq/g, corresponding to the first acidity of the grafted phosphate, and of 1.2 mEq/g, corresponding to the second acidity. This shows a degree of crosslinking of 0.6 mEq of phosphodiester functional groups per gram of crosslinked gel.

EXAMPLE 19

Incorporation of Keratin in SMBV Containing Cationic Nuclei with a Size of 200 nm Keratin is the structural protein of the surface layers of the skin. It is available in the form of soluble partial hydrolyzates with an average molecular weight of approximately 100,000 and with an isoelectric point of between 5.0 and 7.0.

* Preparation of a Cationic Polysaccharide Matrix 2 kg of maize starch (Roquette, Lille, France) are solubilized in 5 l of 2N NaOH in a 30 l reactor. When the solution is homogeneous, 1 kg of glycidyltrimethylammonium chloride, i.e. 0.5 equivalent/glucose residue, dissolved in 500 ml water, is introduced. The preparation is homogenized for a further 2 h, then left standing for 10 h and finally neutralized to a pH of 7 by addition of 2N hydrochloric acid. The gel is then washed several times with distilled water, using a centrifugal dryer, until all the salts and reaction by-products have been removed.

* Preparation of Particles with a Size of 200 nm 1 kg of the gel prepared above is dispersed in 40 l of distilled water and homogenized for 4 h by a Rannie Lab 12-51 homogenizer (APV Rannie, Copenhagen, Denmark) at a pressure of 500 bars and a flow rate of 120 l/h.

Analysis of the size of the particles obtained is carried out using a Coulter N4 nanosizer and shows that the dispersion is centered on a mean size of 200 nm.

These particles are then dried using an APV Lab 1 atomizer in the presence of ammonium bicarbonate (50 g/l).

* Preparation of the Peripheral Lipid Layer 200 g of dried particles are dispersed in 2.5 l of dichloromethane. 30 g of palmitoyl chloride are added. The reaction mixture is stirred overnight. The dichloromethane is then filtered and the residue is then washed several times with dichloromethane, then with ethanol and finally dried under vacuum. The degree of grafted fatty acids, measured after saponification, is 0.8%.

* Charging Keratin to the Cationic Polysaccharide Particles 200 g of acylated polysaccharide nuclei are slowly rehydrated with 1 l of a solution containing 400 g/l of keratin soluble hydrolyzate (Croda) with slow stirring and then 2 l of distilled water are added. At the end of 8 h, 10 g of hydrogenated soya phosphatidylcholine (Nattermann, France) are added and the mixture is left to stir for 1 h. The suspension is injected into 17 of distilled water and homogenized in a Rannie Lab 12-51 homogenizer (APV Rannie, Copenhagen, Denmark) at a pressure of 300 bars for 1 h at a flow rate of 120 1/h.

The suspension thus obtained is analyzed in order to determine the size of the particles, using a Coulter N4 nanosizer. The dispersion is centered around 160 nm. Ultrafiltration of the suspension, followed by quantitative determination of the total proteins using the Bradford method, shows the presence of 80 g of keratin in the ultrafiltrate, i.e. an encapsulation yield of 80% and a degree of charging of 160% with respect to the weight of acylated nuclei.

EXAMPLE 20

Preparation of SMBV Characterized by a Central Starch Nucleus Co-Crosslinked with Keratin 200 g of soluble starch (Prolabo, Paris, France) and 20 g of keratin soluble hydrolyzate are dispersed in 3 l of 2N NaOH in a 5 l reactor. When the solution is homogeneous, 9.7 ml of epichlorohydrin, corresponding to 0.1 equivalent/glucose residue, are added. The preparation is homogenized for 2 h, then left standing for 10 h and finally neutralized to a pH of 7 by addition of 2N acetic acid. The gel is then washed several times with distilled water, using a centrifugal dryer, until all the salts and reaction by-products have been removed. This polysaccharide gel is then dispersed in 4 l of distilled water and homogenized for 4 h with a Rannie Mini Lab homogenizer (APV Rannie, Copenhagen, Denmark) at a pressure of 600 bars and a flow rate of 10 l/h.

Analysis of the size of the particles obtained is carried out using a Coulter N4 nanosizer and shows that the dispersion is centered on a mean size of 210 nm.

Elemental microanalysis shows a nitrogen proportion of approximately 1.1% of the total weight, i.e. a keratin/polysaccharide co-crosslinking yield greater than 95%.

These particles are then dried by atomization or by freeze drying in the presence of ammonium bicarbonate (50 g/l), acylated and dispersed in the hydrogenated soya phosphatidylcholine lamella according to the procedures described in Example 19. The dispersions thus obtained are centered around a size of 190 nm.

EXAMPLE 21

Establishment of an External Amphiphilic Lamella Composed of Ceramides

A suspension of 2.5 g of ceramides (Bio Europe, Toulouse, France) in 5 l of distilled water is homogenized by a Rannie homogenizer at 300 bars for 15 minutes at a flow rate of 10 l/h.

50 g of acylated polysaccharide nuclei, prepared according to Example 19, are progressively added to this suspension, while maintaining the pressure of 300 bars, and then homogenized for 3 h. The dispersion obtained is analyzed using a Coulter N4 nanosizer and the mean size is measured at 230 nm.

We claim:

1. A nucleus particle for use in forming a vector, said particle consisting of a cross-linked polysaccharide or oligosaccharide matrix, onto which ionic ligands are grafted with a uniform distribution, having a size of between 10 nm and 10 μm, which particle is obtained by a method comprising the steps of:

a) preparing a matrix by reacting a biodegradable polysaccharide or oligosaccharide in aqueous medium with a phosphoric acid or derivative thereof whereby said phosphoric acid or derivative provides cross-linking of the polysaccharide or oligosaccharide and grafting of ionic ligands onto the polysaccharide or oligosaccharide to obtain said matrix as said nucleus for use in forming a vector, and b) subjecting the nucleus to grinding to reduce it to a size between 10 nm and 10 µm to obtain said particle.

2. The particle as claimed in claim 1, wherein said particle is the nucleus of a vector entrapping a molecule having biological activity.

3. The particle as claimed in claim 1, wherein said cross-linking comprises co-cross-linking said polysaccaride or oligosaccharide with a protein or a peptide.

4. The particle as claimed in claim 3, wherein the protein is selected from the group consisting of keratin, collagen, elastase, their derivatives and their analogs.

5. The particle as claimed in claim 1, wherein a derivative of phosphoric acid is used and the derivative is phosphorous oxychloride.

6. A method of synthesizing a biodegradable particulate vector, said method comprising the steps of:

(a) preparing a matrix by reacting a biodegradable polysaccharide or oligosaccharide with a phosphoric acid or derivative thereof dissolved in an aqueous medium whereby said phosphoric acid or derivative provides cross-linking of the polysaccharide or oligosaccharide and grafting of ionic ligands onto the polysaccharide or oligosaccharide to obtain said matrix as a nucleus of the vector, (b) subjecting the nucleus to grinding to reduce it to a size between 10 nm and 10 µm, (c) drying the nucleus, (d) chemically coupling fatty acid compounds to reactive functional groups at the surface of the nucleus to form a first layer of the vector, and (e) hydrophobically bonding amphiphilic compounds wherein said amphiphilic compounds are phospholipids, by bringing them into contact with the first layer to form a second layer of the vector.

7. The method as claimed in claim 6, wherein a derivative of phosphoric acid is used and the derivative is phosphorous oxychloride.

8. The method as claimed in claim 6, wherein after step d) and before step e), a molecule having biological activity is added to the nucleus.

9. The method as claimed in claim 8, wherein the molecule having biological activity is added by mixing and hydrating the molecule with the nucleus obtained at the end of step d).

10. The method as claimed in claim 8, wherein the molecule having biological activity is a non-ionic compound having an ionic charge reversibly grafted thereon.

11. The method as claimed in claim 6, wherein step c) is carried out in the presence of ammonium bicarbonate.

12. The method as claimed in claim 6, wherein steps c) and d) are repeated at least once and a hydration step is performed between repetitions.

13. The method as claimed in claim 6, wherein step d) is carried out in $CO_2$ in the super-critical state.

14. The method as claimed in claim 6, wherein in step e) the amphiphilic compounds are brought into contact with the first layer in a solution containing a detergent, followed by removal of the detergent by dialysis.

15. The method as claimed in claim 6, wherein said phospholipids are ceramides.

16. A particulate vector prepared by the method of claim 6.

17. A particulate vector prepared by the method of claim 7.

18. The particulate vector as claimed in claim 16, wherein the ionic ligand is is grafted in an amount ranging up to one charge per 1.5 glucose residues.

19. The particulate vector as claimed in claim 16, wherein the polysaccharide or oligosaccharide is selected from the group consisting of dextran, starch, cellulose and their derivatives.

20. The particulate vector as claimed in claim 16, wherein said cross-linking comprises co-cross-linking said polysaccharide or oligosaccharide with a protein or a peptide.

21. The particulate vector as claimed in claim 20, wherein the protein is selected from the group consisting of keratin, collagen, elastase, their derivatives and their analogs.

22. The particulate vector as claimed in claim 16, wherein the fatty acids of the first layer of the vector are natural fatty acids which are covalently bound to the reactive functional groups.

23. The particulate vector as claimed in claim 16, wherein the second layer is formed of a double phospholipid lamella having an internal lamella interdigitated by the fatty acids of the first layer.

24. A particulate vector prepared by the method of claim 8.

25. The particulate vector as claimed in claim 24, wherein the molecule having biological activity has a molecular weight between 100 daltons and 500 kilodaltons.

* * * * *